United States Patent
Takashima

(10) Patent No.: US 6,589,193 B2
(45) Date of Patent: Jul. 8, 2003

(54) HEMORRHOID TREATMENT AND PROSTATE MASSAGE APPARATUS

(76) Inventor: Jiro Takashima, 7203 Schiller, Houston, TX (US) 77055

( * ) Notice: Subject to any disclaimer, the term of this patent is extended or adjusted under 35 U.S.C. 154(b) by 0 days.

(21) Appl. No.: 09/883,900

(22) Filed: Jun. 19, 2001

(65) Prior Publication Data
US 2002/0040200 A1 Apr. 4, 2002

Related U.S. Application Data

(63) Continuation-in-part of application No. 09/675,436, filed on Sep. 29, 2000.

(51) Int. Cl.[7] .............................................. A61H 19/00
(52) U.S. Cl. ....................................... 601/137; 606/197
(58) Field of Search ........................ 606/191, 197–198; 128/61, 62; 601/137

(56) References Cited

U.S. PATENT DOCUMENTS

| 547,076 | A | * | 1/1895 | Hubbell |
| 2,485,939 | A | * | 10/1949 | Tedford |
| 2,974,666 | A | * | 3/1961 | Coumbis et al. |
| 3,675,642 | A | * | 7/1972 | Lord |
| 4,583,542 | A | * | 4/1986 | Boyd |
| 4,938,221 | A | * | 7/1990 | Tuffel |
| 5,797,950 | A | * | 8/1998 | Takashima |
| 5,861,000 | A | * | 1/1999 | Takashima |

\* cited by examiner

Primary Examiner—Nicholas D. Lucchesi
Assistant Examiner—Lalita M. Hamilton
(74) Attorney, Agent, or Firm—Harrison & Egbert

(57) ABSTRACT

An apparatus for massaging a prostate gland and for providing treatment for hemorrhoids through the contraction of a human sphincter including a head having a size suitable for fitting into a human rectum and through the sphincter and a resistor connected to a bottom of the head. The head has a bulbous upper portion and a tapered section extending from the upper portion. The tapered section narrows in diameter from the upper portion of the head. The resistor has a spindle shape with a first tapered surface widening from the bottom of the head so as to define a wide section of the resistor. The resistor has a second tapered surface extending and narrowing from the wide section of the first tapered surface.

4 Claims, 3 Drawing Sheets

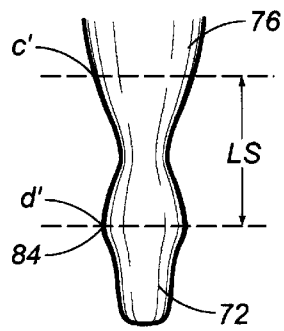
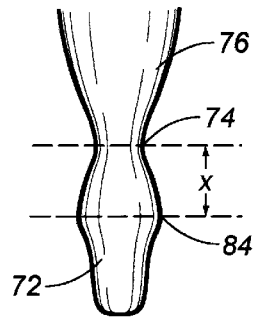
FIG. 5A  FIG. 5B
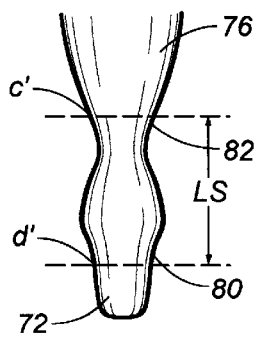
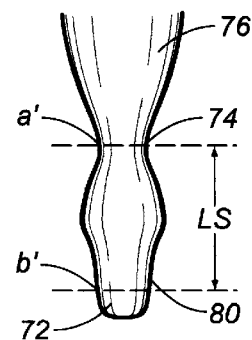
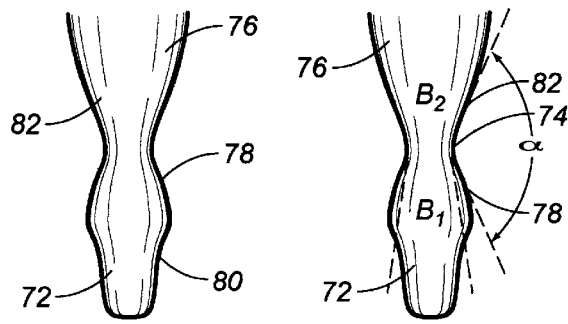
FIG. 5C  FIG. 5D  FIG. 5E  FIG. 5F
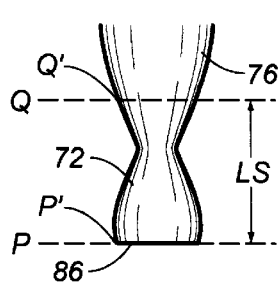
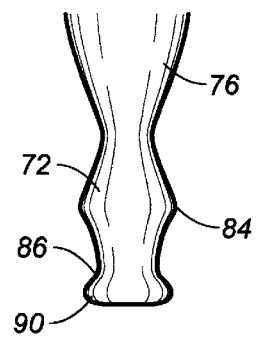
FIG. 5G  FIG. 5H

HEMORRHOID TREATMENT AND PROSTATE MASSAGE APPARATUS

CROSS REFERENCE TO RELATED APPLICATIONS

The present application is a continuation-in-part of U.S. patent application Ser. No. 09/675,436, filed on Sep. 29, 2000, and entitled "PROSTATE MASSAGE APPARATUS", presently pending.

BACKGROUND OF THE INVENTION

1. Field of the Invention

The present invention relates to apparatus for the treatment of hemorrhoids. More particularly, the present invention relates to apparatus for the treatment of prostatitis. More particularly, the present invention relates to plug-type apparatus that can be inserted through the human rectum for the massaging of the prostate gland and for the treatment of hemorrhoids.

2. Description of Related Art

One treatment for non-bacterial disorders of the prostate such as chronic prostatitis and a congested prostate is the prostate massage. Some urologists believe that the most effective treatment for such prostatitis is for the doctor to massage the prostate at regular intervals. Other urologists are far less enthusiastic about this procedure, and some do not believe in it at all. To perform such a massage, the physician simply inserts a gloved finger into the rectum and strokes the prostate very gently. It serves to relieve the symptoms of chronic prostatitis by draining accumulated prostatic fluid from the glands and ducts.

Given the difference of opinion of urologists as to the need for prostatic massages, such massages can be difficult to obtain. In any event, the regular and repeated massaging of the prostate can often require frequent visits to the doctor's office. This causes the patient to incur a considerable expense and inconvenience. As such, a need has developed for allowing an individual to carry out his own prostatic massage.

In the past, some patents have issued relating to rectal devices. U.S. Pat. No. 4,542,753, issued on Sep. 24, 1985 to Brenman et al. describes an apparatus and method for stimulating penile erectile tissue. In this invention, a body is provided which may be inserted into the rectum of a user. The body is shaped so as to closely conform to the topological configuration of the rectum within the anal area to a site adjacent to the prostate gland. Electrical circuitry for generating a neurally stimulating electrical signal is located within the body. Electrodes, placed at particular locations on the surface of the body, apply the signal to the user. At least one of the electrodes closely contacts the prostate gland when the body member is operatively disposed, at a region or spot on the prostate gland previously determined to be sensitive to electrical stimulation.

U.S. Pat. No. 5,404,881, issued on Apr. 11, 1995, to Cathaud et al. describes a trans-rectal probe. This trans-rectal probe includes a probe body made of a flexible self-supporting polymer material whose degree of flexibility is designed to enable it to comply with the shape of the rectum while having substantially no compression effect on the rectum when inserted therein. The invention makes it possible to achieve accurate, safe and reliable positioning or an instrument for detection or therapeutic treatment level with the organ to be observed or treated. In particular, this device is designed for treatment of the prostate.

U.S. Pat. No. 2,478,786, issued on Aug. 9, 1949 to H. M. Smallen, describes a prostate gland massaging implement. This implement includes a lever having an interior handle which constitutes a power arm to extend down in front of the abdomen and a substantially horizontal portion extending under the groin and offset laterally to avoid the genital organs. The implement has an upwardly and forwardly bent posterior portion which forms the work arm. This work arm extends into the rectal passage to bear across the frontal wall thereon adjacent the prostate gland. The bent portion between the horizontal and the posterior portions serves as a fulcrum point against the front wall of the rectal opening when the implement is subject to pivotal movement around this point The present inventor has two United States patents showing devices for releasing congested prostate fluid. U.S. Pat. No. 5,797,950, issued on Aug. 25, 1998, describes such a device including a head having a size suitable for fitting in a human rectum and through a sphincter. The head has a size suitable for rubbing the prostate gland. A rod is connected to the bottom of the head and extends outwardly therefrom. The rod serves to position the head and guide a movement of the head as the sphincter contracts and relaxes. An abutment surface is affixed to the rod distal the head. The abutment surface contacts the perineum area and pushes up on the perineum area as the sphincter contracts. The rod is a rigid rod having a generally L-shaped or C-shaped configuration with a radius of curvature such that the head tilts toward the prostate gland as the sphincter contracts and draws the head upwardly. The head has a generally ellipsoidal shape.

U.S. Pat. No. 5,861,009, issued on Jan. 19, 1999, to the present inventor, describes an apparatus for releasing congested prostate fluid having a head with a size suitable for fitting into a human rectum and through the sphincter and having a surface for pushing on the prostate gland. A rod is connected to the bottom of the head and extends outwardly therefrom so as to guide a movement of the head as the sphincter relaxes and contracts. An abutment member is positioned on the rod opposite the head so as to push on the perineum area simultaneously with the head pushing on the prostate gland. The abutment member has a variable angular relationship with the head.

In each of these prior art patents to the present inventor, the rod movably holds the head within the sphincter, and when the external sphincter contracts, the lateral pressure of the external sphincter drives the head upwardly and the rod adds pressure against the perineum area simultaneously. The power of the sphincter's contraction is divided into one for pressure on the prostate and one for pressure onto the perineum area. Under certain circumstances, some persons have felt that the perineum pressure by this rod was strong and uncomfortable.

It is an object of the present invention to provide an apparatus which enables persons to carry out self-massages of the prostate so as to express the fluid from this congested prostate.

It is a further object of the present invention to provide a prostate massage apparatus which reduces or even eliminates the amount of pressure applied to the perineum area while maintaining the tapered portion of the head and resistor combination movably within the sphincter.

It is a further object of the present invention to provide a prostate massage apparatus that the head and the resistor combination within the sphincter canal induces the peristaltic movement of the surface of the sphincter muscles so as to cause energy consumption inside the sphincter for increasing blood circulation of the area.

It is a further object of the present invention to provide a prostate massage apparatus which increases blood flow for treating hemorrhoidal symptoms.

It is a farther object of the present invention to provide such a prostate massage apparatus which is safe, easy to use and relatively inexpensive These and other objects and advantages of the present invention will become apparent from a reading of the attached specification and appended claims.

BRIEF SUMMARY OF THE INVENTION

The present invention is an apparatus for massaging a prostate gland by contraction of a human sphincter comprising a head having a size suitable for fitting into a human rectum and through the sphincter and a resistor connected to a bottom of the head. The head has a bulbous upper portion and a tapered section extending from the upper portion. The tapered section narrows in diameter from the upper portion. The resistor has a spindle shape with a first tapered surface widening from the bottom of the head so as to define a wide section of the resistor. The resistor has a second tapered surface extending and narrowing from the wide section of the first tapered surface.

In the present invention, the wide section has a diameter which is between 90 and 110 percent of a diameter of the head at a location spaced by a length of the sphincter from the wide section of the resistor. The bottom of the head is spaced from the wide section of the resistor by less than the length of the sphincter. The tapered section of the head has a diameter equal to a diameter of the second tapered surface of the resistor at a distance equal to the length of the sphincter. The bottom of the head has a diameter which is smaller than a diameter of the second tapered surface of the resistor at a distance from the bottom of the head equal to the length of the sphincter. The head and the resistor have a combined length of less than four inches. The resistor has a length which is less than the length of the sphincter.

The first tapered surface of the resistor has an angle of taper which is narrower than an angle of taper of the tapered section of the head. The tapered section of the head and the first tapered surface of the resistor are spaced from each other by between 130° and 172°. The angle of taper of the first tapered surface of the resistor and the angle of taper of the tapered section of the head have a difference of no more than three times. The resistor has a bottom which has a diameter which is between 90% and 110% of a diameter of the tapered section of the head at a location spaced from the bottom of the resistor by the length of the sphincter.

In an alternative embodiment of the present invention, the resistor has a bottom with a diameter which is 90% to 110% of the diameter of the wide section of the resistor.

A rod can be affixed to the bottom of the resistor opposite to the head and extend outwardly therefrom for the treatment of the perineum area.

BRIEF DESCRIPTION OF THE SEVERAL VIEWS OF THE DRAWINGS

FIGS 5(A)–(H) show the various dimensional relationships between the head portion and the resistor portion of the prostate massage apparatus of the present invention.

DETAILED DESCRIPTION OF THE INVENTION

Figure 1:
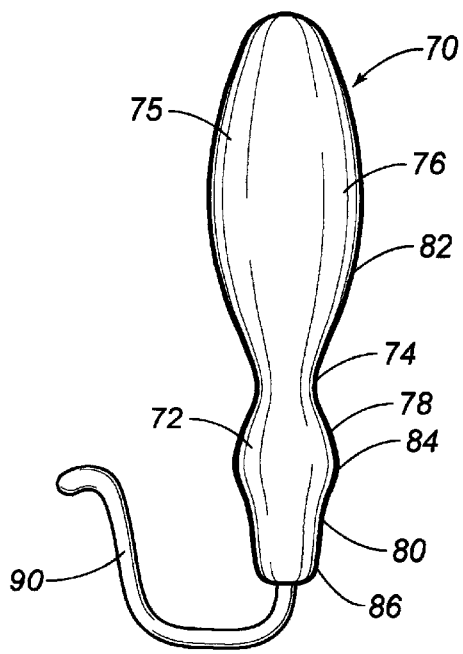
FIG. 1 shows a side elevational view of the preferred embodiment of the prostate massage apparatus of the present invention.

FIG. 1 shows the prostate massage apparatus 70 of the present invention. The prostate massage apparatus 70 includes a head 76 and a resistor section 72. The resistor section 72 is connected to the bottom 74 of the head 76. The head 76 has a size suitable for fitting into a human rectum and through the sphincter. The head 76 has a bulbous upper portion 75 and a tapered section 82 extending from the upper portion 75. The tapered section 82 narrows in diameter from the upper portion 75.

The resistor 72 has a spindle shape with a first tapered surface 78 and a second tapered surface 80. The first tapered surface 78 tapers outwardly so as to widen from the bottom 74 of the head 76 to the wide section 84 at the bottom of the first tapered section 78 on the resistor 72. The second tapered surface 80 narrows from the wide section 84 of the resistor 72 toward the bottom 86 of the resistor 72. A rod 90 is connected to the bottom of the resistor 72.

Figure 2:
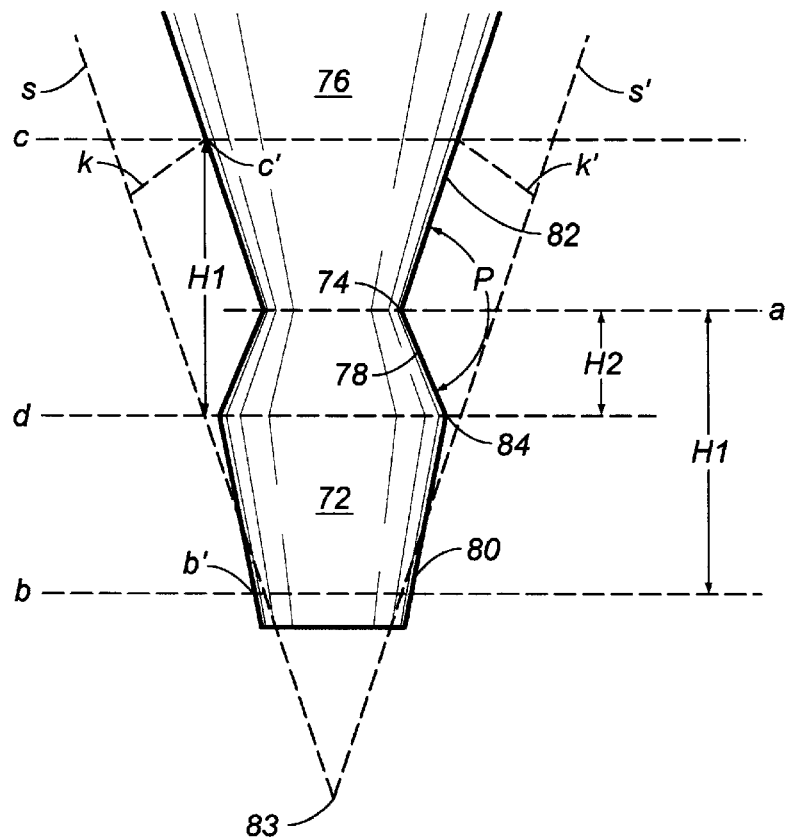
FIG. 2 shows an enlarged diagrammatic illustration of the relationship between the resistor section and the bottom of the head portion of the prostate massage apparatus of the present invention.

FIG. 2 shows some of the dimensional relationships between the head 76 and the resistor 72. The broken line (a) extends across the bottom 74 of the head 76. The broken line (b) is a transverse line which is positioned below the broken line (a) by a distance equal to the length of the sphincter (H1). Conventionally, in human bodies, the sphincter will have a length of between 1 and 1½ inches. The broken line (d) is a transverse line extending across the wide section 84 of the resistor 72. The broken line (c) is a transverse line which is positioned above the broken line (d) by the length of the sphincter (H1). The broken lines (s) and (s') are lines which extend parallel to the tapered surface 82 on the head 76. Broken lines (s) and (s') will intersect broken line (d) at a desired location and will intersect each other at point 83. The broken lines (s) and (s') are spaced from the tapered surface 82 of the head 76 by a distance shown by broken line (k) and (k'). The diameter of the resistor 72 at any location within the broken line (s) and (s') will have a smaller diameter than the diameter of the head 76 at a location greater than the length of the sphincter (H1). Similarly, the diameter of the resistor 72 at any location out side the broken lines (s) and (s') will have a greater diameter than the head 76 at any location along the head 76 within the length of the sphincter H1.

The second tapered surface 80 of the resistor 72 has a narrower tapered angle than the tapered surface 82 of the head 76. As can be seen, there is a portion of the second tapered section 80 of the resistor 72 that crosses the broken lines (s) and (s') so as to reside outside of the lines (s) and (s'). The section of the resistor 72 at point (b') is located on the resistor at a length equal to the length of the sphincter (H1) from the bottom 74 of the head 76. Thus, the diameter of the bottom 74 of the head 76 is slightly less than the diameter of the resistor at the location (b'). The diameter of the resistor 72 at (b') is greater than the diameter of the head 76 at the bottom 74.

If the resistor 72 is shorter than the length of the sphincter, the diameter of the bottom 86 of the resistor 72 will be slightly larger than the diameter of the diameter of the section of the head 76 will have a location equal to the length of the sphincter (H1) from the bottom 86 of the resistor 72.

The wide section 84 of the resistor 72 is located just within the broken lines (s) and (s'). This means that the diameter of the wide section 84 of the resistor 72 will be slightly smaller than the diameter of the head 76 at the section (c'). Section (c') is located at a distance from the wide section 84 of the resistor 72 by the length of the sphincter (H1).

The distance (H2) between the bottom 74 of the head 76 and the wide section 84 of the resistor 72 is less than the length of the sphincter (H1). Distance (H2) is greater than ¼ of the length of the sphincter (H1) and shorter than ¾ of the length of the sphincter (H1).

For effective and smooth operation, the angle (p) between the tapered surface 82 of the head 76 and the first tapered surface 78 of the resistor 72 is greater than 130 degrees and narrower than 172 degrees. The angle of taper of the tapered surface of the 82 of the head 76 and the angle of taper of the first tapered surface 78 of the resister 72 will have a difference of no more than three times each other.

Figure 3:
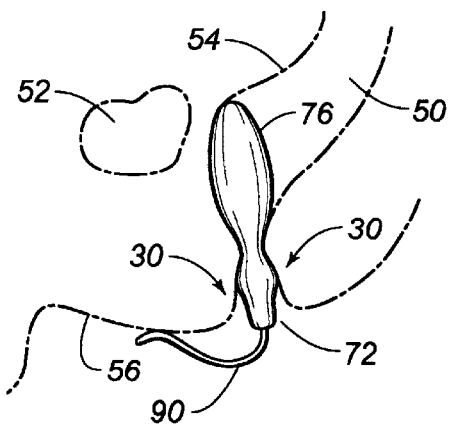
FIG. 3 shows the action of the prostate massage apparatus as located within a human rectum.

FIG. 3 illustrates the prostate massage apparatus 70 as located within the rectum 50. In FIG. 3, it can be seen that the head 76 has been inserted into the rectum 50 through the sphincter 30. The head 76 is positioned by the rod 90 in proximity to the prostate 52. The prostate 52 is pressed through the wall 54 of the rectum 50. As shown in FIG. 3, the rectum 50 turns backwardly from between 3½ to 4 inches from the entrance of the sphincter 30. For effective massage, the total length of the combined head 76 and the resistor 72 should be shorter than four inches. If the combined length of the head 76 and the resistor 72 is greater than four inches, the turning point of the wall of the rectum 50 will interfere with the free movement of the apparatus 70 within the rectum 50.

The rod 90 extends outwardly through the sphincter 30 and wraps across to the perineum area 56. The rod 90 can be configured so as to movably hold the tapered portion 82 of the head 76 within the sphincter 30 and apply pressure to the perineum area 56 at the same time that the head 76 is massaging the prostate 52. As such, the apparatus 70 massages the prostate and also provides for stimulation at the perineum area 56. Unlike the prior patents (U.S. Pat. Nos. 5,797,950 and 5,861,000) to the present inventor, the pressure applied to the perineum area 56 can be reduced or eliminated because of the counter-pressure provided by the resistor 72 relative to the sphincter 30. The consumption of the energy within the sphincter 30 is increased so as to result in greater blood circulation in the area. Experimentation with the present invention has found the present invention is very effective in the treatment of hemorrhoidal conditions. The increased blood flow into the area greatly reduces the hemorrhoids symptoms.

Figures 4A, 4B, 4C:
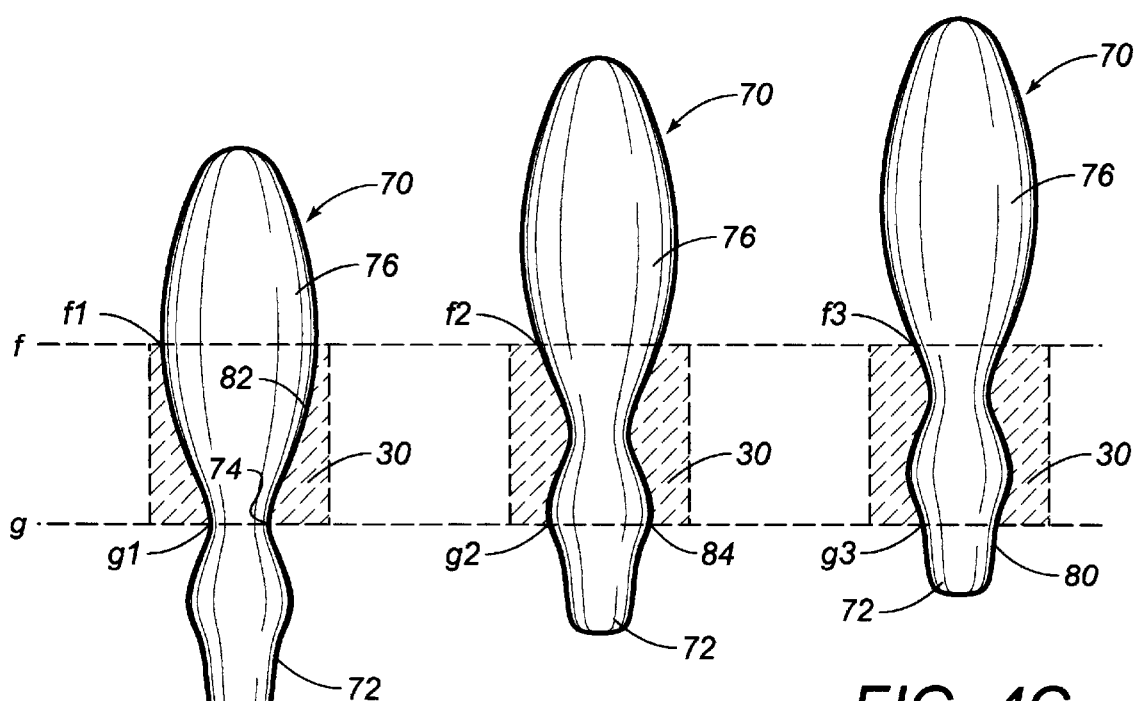
FIGS. 4(A)–(C) shows the movement of the prostate massage apparatus of the present invention within the human sphincter.

FIGS. 4(A)–(C) show the operation of the apparatus 70 as located within the sphincter. The broken line (f) illustrates the upper edge of the sphincter 30. The broken line (g) illustrates the lower edge of the sphincter. In FIG. 4(A), the first position of the apparatus 70 is particularly illustrated. Apparatus 70 is inserted into the sphincter 30. The lateral pressure of the sphincter 30 onto the tapered surface 82 of the head 76 forces the apparatus 70 upwardly. The bottom 74 of the head 76 will be positioned against the lower edge (g1) of the sphincter 30. The diameter of the head 76 as positioned at position (f1) is wider than the diameter of the apparatus 70 at g1. Lateral pressure of the sphincter 30 continues to force the apparatus 70 upwardly. The section of the head spaced by the length of the sphincter 30 from the wide section 84 of the resistor 72 is set so that when the sphincter 30 contracts, the wide section 84 of the resistor 72 barely passed through the lower edge g2 of the sphincter 30. To achieve this condition by the lateral pressure of the sphincter 30 alone, the diameter at the wide section 84 of the resistor 72 needs to be slightly smaller than the corresponding section of the head 76 located at (f2). In certain situations, it is necessary to set the diameter of the wide section 84 of the resistor 72 slightly larger than the corresponding diameter of the section of the head 76 at (f2). Peristaltic movement of the surface of the sphincter muscles will also force the resistor 72 upwardly.

FIG. 4(C) shows how the diameter of the head 76 at the upper edge (f3) of the sphincter 30 equals the diameter of the section of the second tapered surface 80 of the resistor 72 at the lower edge (g3) of the sphincter 30. The lateral pressure of the sphincter 30 alone is no longer able to push up or down the apparatus 70 from this position. The body's natural reaction is to retract the resistor 72 inside the rectum 50 by peristaltic movement of the surface of the sphincter 30. As a result, the diameter of the head 76 at section (f3) is narrower than the section of the resistor 72 at the lower edge (g3) of the sphincter 30. As a result, the lateral pressure of the sphincter 30 forces the resistor 72 downwardly. The diameter of the section of the head 76 at the upper edge (f3) of the sphincter 30 becomes wider than the section of the second tapered surface 80 of the resistor 72 at the lower edge (g3) of the sphincter. As a result, the lateral force of the sphincter 30 forces the resistor upwardly. This subtle up-and-down movement of the resistor 72 within the sphincter 30 will continue constantly. The movement of the apparatus 70 as forced by the peristaltic movement of the surfaces of the sphincter 30 and the lateral pressure of the sphincter 30 gives good massage effects to those muscles. The surface of the sphincter 30 will have good blood circulation so as to further improve hemorrhoidal conditions.

FIG. 5(A), it can be seen that the diameter (d') at the wide section 84 of the resistor 72 is between 90% to 110% of the diameter of the head 76 at (c'). The section at (c') is separated from the wide section 84 of the resistor 72 at (d') by the length of the sphincter (LS).

FIG. 5(B) illustrates that the bottom 74 of the head 76 is separated by a distance X from the wide section 84 of the resistor 72. Distance X will be less than the length of the sphincter LS. In the present invention, distance between the bottom 74 of the head 76 and the wide section 84 of the resistor 72 from the bottom 74 will be less than the length of the sphincter.

FIG. 5(C) shows that the diameter at (c') of the tapered surface 82 of the head 76 is separated from a section (d') at the second tapered surface 80 of the resistor 72 by the length of the sphincter (LS). The diameter at section (d') will be equal to the diameter at section (c') so as to create a balanced position of the apparatus 70 within the sphincter 30.

FIG. 5(D) shows that the diameter at section (a') at the bottom 74 of the head 76 is slightly smaller than the diameter at section (b') located on the second tapered surface 80 of the resistor 72. Section (a') is separated by section (b') by the length of the sphincter LS. Alternatively, section (b') can have a diameter which is between 90 and 110% of the diameter at section (a') at the bottom 74 of the head 76.

FIG. 5(E) shows that the tapered surface 82 and the head 76 has an angle of taper which is wider than the angle of taper of the second tapered surface 80 of the resistor 72.

FIG. 5(F) shows that the tapered surface 82 of the head 76 is separated from the first tapered surface 78 of the resistor 72 by an angle α. The angle α should be greater than 130° but narrower than 172°. FIG. 5(F) shows that the resistor 72 has an average angle of taper $B_1$. The head 76 will have an average angle of taper $B_2$. Angle of taper $B_1$ and angle of taper $B_2$ should be no more than three times each other.

FIG. 5(G) illustrates the circumstance in which the resistor 72 has a length which is shorter than the length of the sphincter LS. The diameter at the bottom 86 of the resistor 72 is shown at section (b'). The bottom 86 of the resistor 72 is separated from a section (Q') of the head 76 by a distance equal to the length of the sphincter LS. The diameter of section (b') is between 90% to 110% of the diameter of the section (Q') of the head 76.

FIG. 5(H) shows the situation in which a stop ring 90 formed at the bottom 86 of the resistor 72. The resistor 72 has a wide section 84. The stop ring 90 will have a diameter which is between 90% and 110% of the diameter at the wide section 84 of the resistor 72.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:
1. An apparatus for massaging a prostrate gland by contracting of a human sphincter comprising:
   a head having a size suitable for fitting into a human rectum and through the sphincter, said head having a bulbous upper portion and a tapered section extending from said upper portion, said tapered section narrowing in diameter from said upper portion; and
   a resistor connected to a bottom of said head, said resistor having a spindle shape with a first tapered surface widening from said bottom of said head so as to define a wide section of said resistor, said resistor having a second tapered surface extending and narrowing from said wide section of said first tapered surface, said tapered section of said head having a diameter dimension which is equal to a diameter dimension on said second tapered surface of said resistor where said diameter dimensions are separated by a longitudinal distance of between 1 and 1.5 inches.
2. The apparatus of claim 1, said head and said resistor having a combined length of less than four inches.
3. The apparatus of claim 1, said second tapered surface of said resistor having an angle of taper which is not greater than an angle of taper of said tapered section of said head.
4. The apparatus of claim 1, said wide section of said resistor having a diameter that is no more than a diameter of said head at a longitudinal distance of between 1 and 1.5 inches from said wide section of said resistor.

* * * * *